United States Patent [19]
Yih-Jong

[11] Patent Number: 5,143,056
[45] Date of Patent: Sep. 1, 1992

[54] MASSAGING SLEEVE WITH MAGNETIC PROTUBERANCES

[76] Inventor: Chang Yih-Jong, P.O. Box 82-144, Taipei, Taiwan

[21] Appl. No.: 737,661

[22] Filed: Jul. 30, 1991

[51] Int. Cl.⁵ .................................. A61H 15/00
[52] U.S. Cl. ........................ 128/57; 128/24 R; 128/62 R
[58] Field of Search ................. 128/57-62, 128/33, 24 R

[56] References Cited
U.S. PATENT DOCUMENTS 3,888,241 6/1975 Fischer ........................ 128/57

Primary Examiner—Robert A. Hafer
Assistant Examiner—David J. Kenealy
Attorney, Agent, or Firm—Alfred Lei

[57] ABSTRACT

This invention relates to a massaging sleeve and in particular to one which includes a pair of cylindrical members having a body with a flange at both ends, a packing fitted into the recess of the flange, a pair of pads each covered on one of the cylindrical members and a plurality of equidistant holes adapted to receive the protuberances of the cylindrical member, a plurality of magnets each fitted into one of the hollow protuberances of the cylindrical members, and two retainers for connecting the pads and the cylindrical members together.

1 Claim, 5 Drawing Sheets

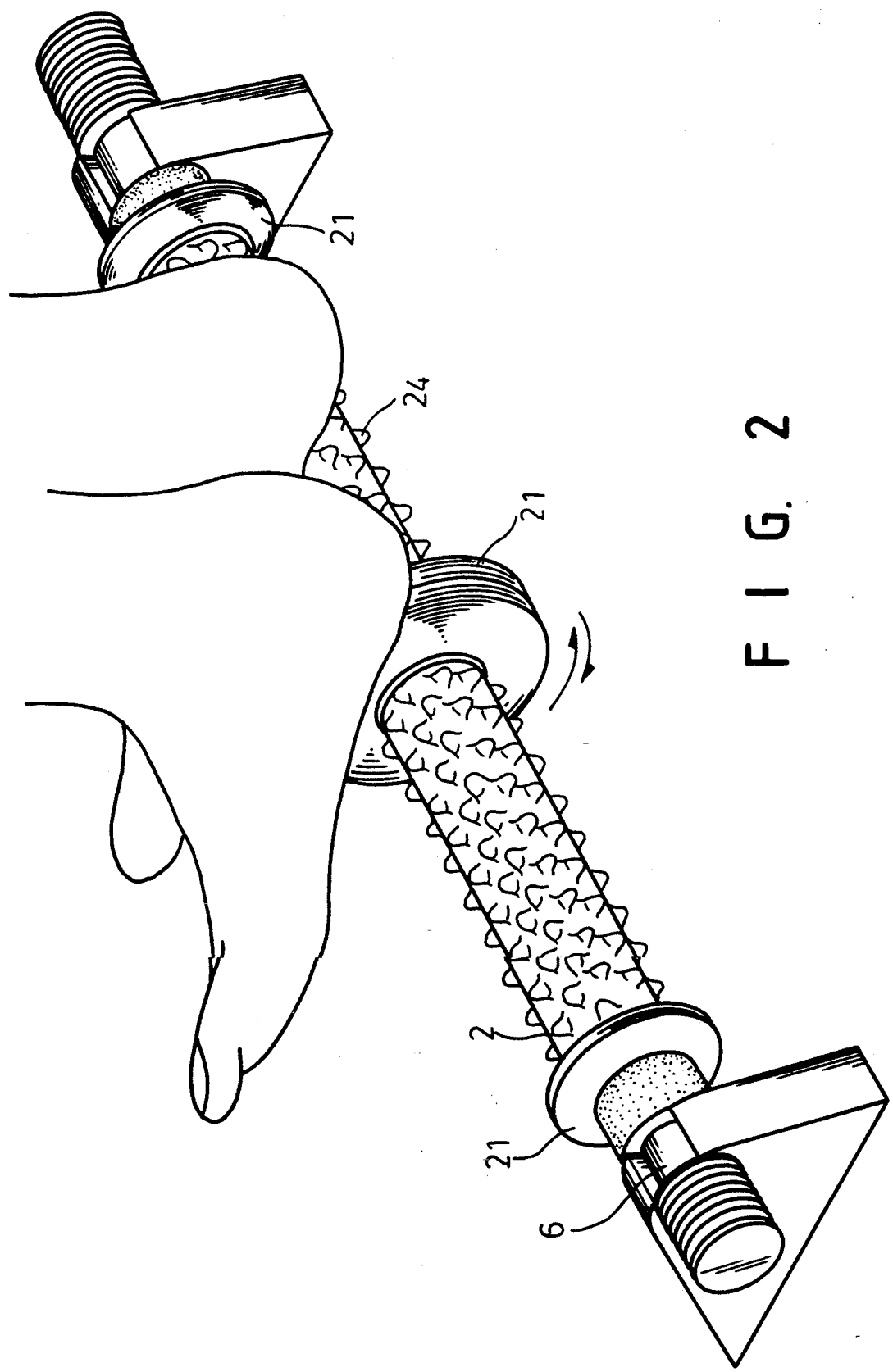

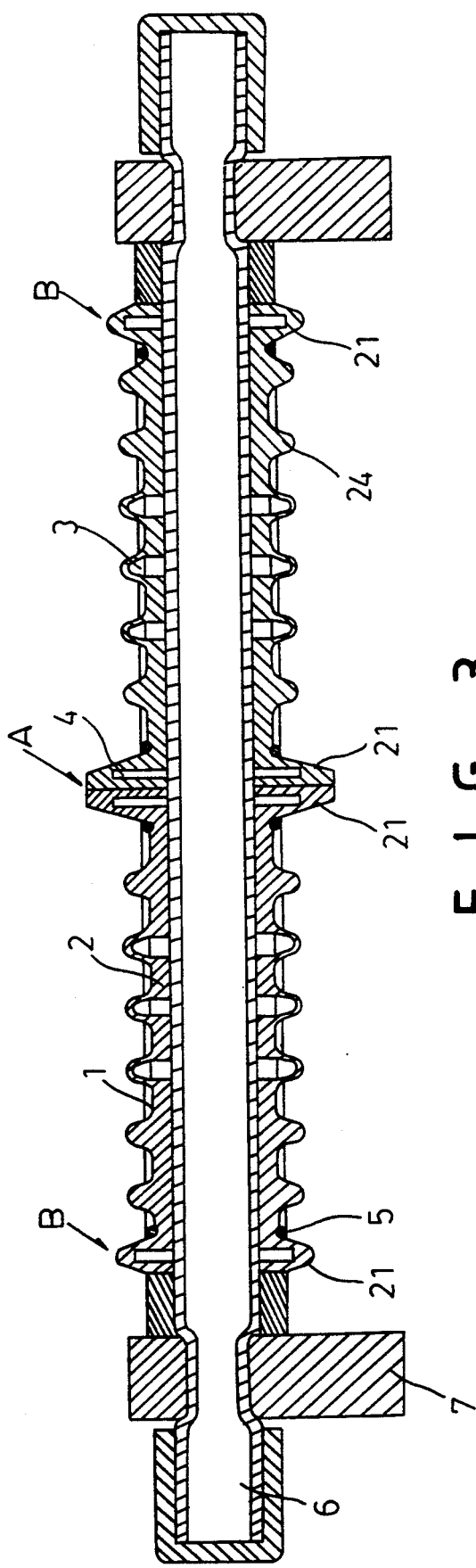
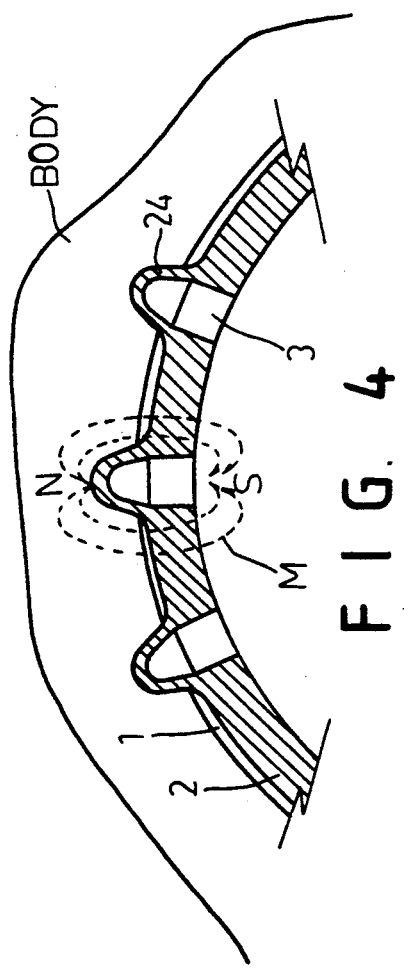

MASSAGING SLEEVE WITH MAGNETIC PROTUBERANCES

BACKGROUND OF THE INVENTION

It is found that the prior art massager with round-headed protuberances on the market cannot provide sufficient stimulation and so it can only be used for finger massager, but not veins and vital points. Further, there is a ball massager which is provided with magnetic protuberances for massage and magnetic remedy on sale, but such a massager is too heavy and inconvenience in use.

Therefore, it is an object of the present invention to provide a massager which may obviate and mitigate the above-mentioned drawbacks.

SUMMARY OF THE INVENTION

This invention relates to a massaging sleeve.

It is the primary object of the present invention to provide a massaging sleeve which may be conveniently fitted to the handle-bar of a motorcycle or bicycle.

It is another object of the present invention to provide a massaging sleeve which may be used to massage the hand of a user even when he rides a motorcycle or bicycle.

It is still another object of the present invention to provide a massaging sleeve which may be used for finger massage as well as magnetic remedy.

It is still another object of the present invention to provide a massaging sleeve which is simple in construction.

It is a further object of the present invention to provide a massaging sleeve which is economic to produce.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2 is a working view of the present invention;

FIG. 3 is a cross-sectional view of the massaging sleeve shown in FIG. 2;

FIG. 4 shows the magnetic remedy principle of the present invention;

DETAILED DESCRIPTION OF THE PREFERRED EMBODIMENT

Figure 1:
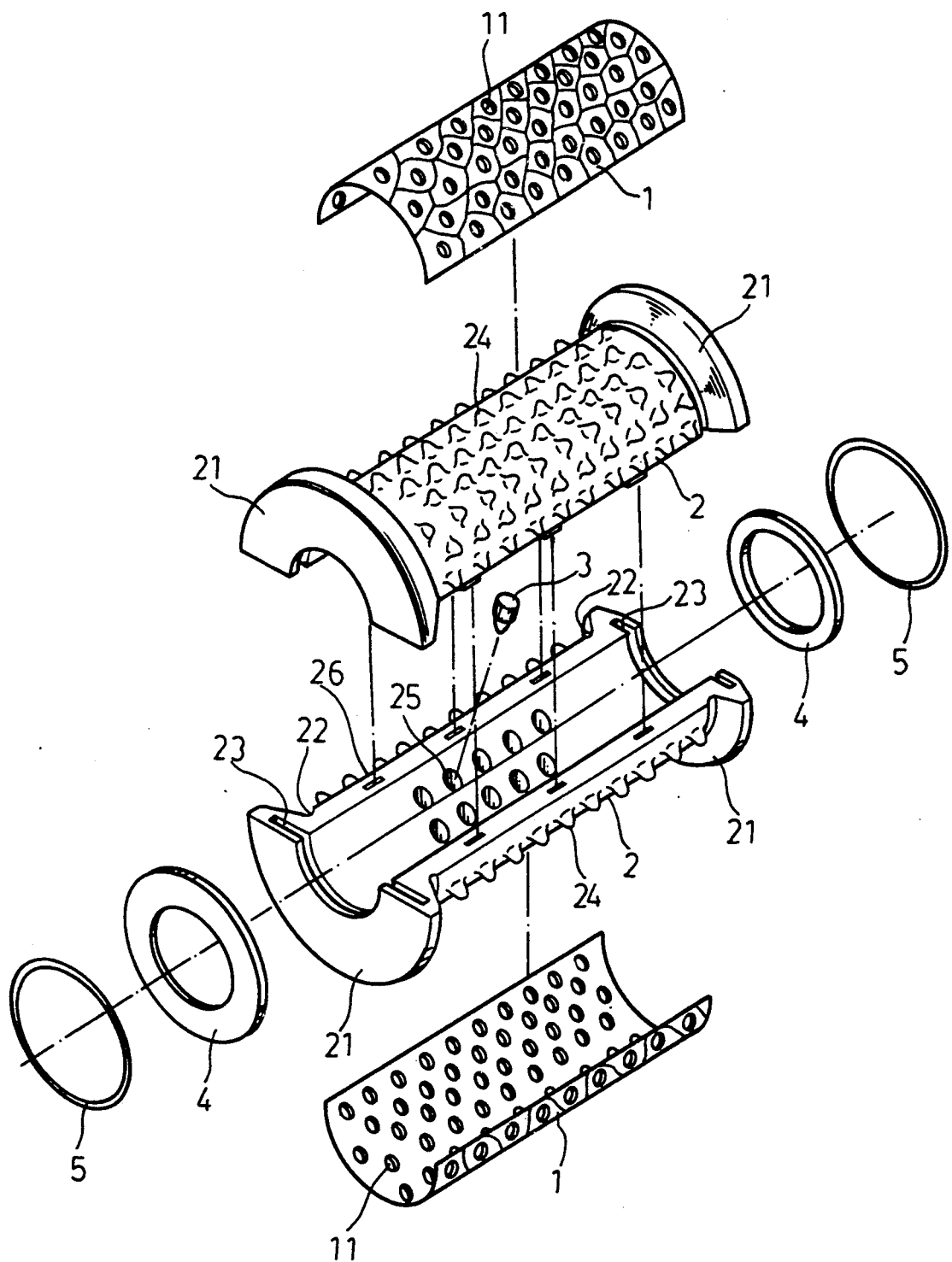
FIG. 1 is an exploded view of a massaging sleeve according to the present invention.

Referring first to FIG. 1, the massaging sleeve according to a preferred embodiment of the present invention mainly comprises a pair of pads 1, a pair of semi-cylindrical members 2, a plurality of magnets 3, two packings 4, and two retainer rings 5. The semi-cylindrical member 2 is made of rubber or plastic with appropriate hardness and is formed with a flange 21 at both ends. Between the body 26 and the flange 21 of the semi-cylindrical member 2 there is a groove 22. Further, the flange 21 is provided with a slot 23 for receiving the packing 4. The upper surface of the body 26 of the semi-cylindrical member 2 has a plurality of equidistant protuberances 24 some of which are solid while others of which are hollow in structure. The solid protuberances 24 are designed for finger massage while the hollow protuberances 24 are provided with a recess 25 for receiving a magnet 3 so as to be used for finger massage as well as magnetic remedy. Further, the pad 1 is used to cover the surface of the semi-cylindrical member 2 and has a plurality of equidistant holes 11 adapted to receive the protuberances 24 of the semi-cylindrical member 2 so as to protect the semi-cylindrical member 2. In addition, the pad 1 may be used to absorb sweat and used as a decoration. The semi-cylindrical members 2 and the pads 1 are connected together by the retainer rings 5.

With reference to FIG. 2, there is shown a working view of the present invention. As illustrated, four cylindrical members 2 are mounted on a shaft 6 both ends of which are supported by a stand 7 thereby forming a sole massager so that the user may use it to massage his sole as shown.

FIG. 3 is the cross sectional view of the massaging sleeve shown in FIG. 2. As may be seen, the portion A is designed to massage the crack between toes or other deep veins and vital points, while the portion B to provide medium massaging effect. Regarding the protuberances 24, they are used to provide massaging effect as well as magnet remedy.

FIG. 4 shows the magnetic effect of the present invention. As shown, when the protuberances 24 of the semi-cylindrical members 2 are used to massage the body, the magnet 3 will magnetize the blood vessels or nerves and produce new electric current in the blood. Hence, the blood circulation is promoted and the cells are activated thereby accelerating metabolism and strenghening the function of the self disciplined nerves.

Figure 5:
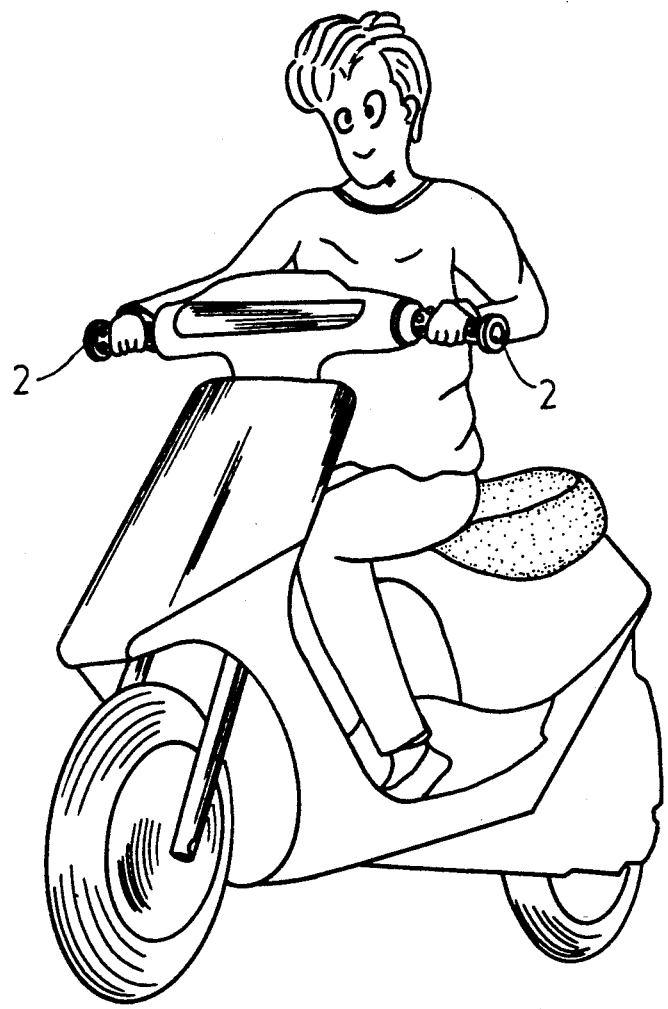
FIG. 5 is a second working view of the present invention.
Figure 6:
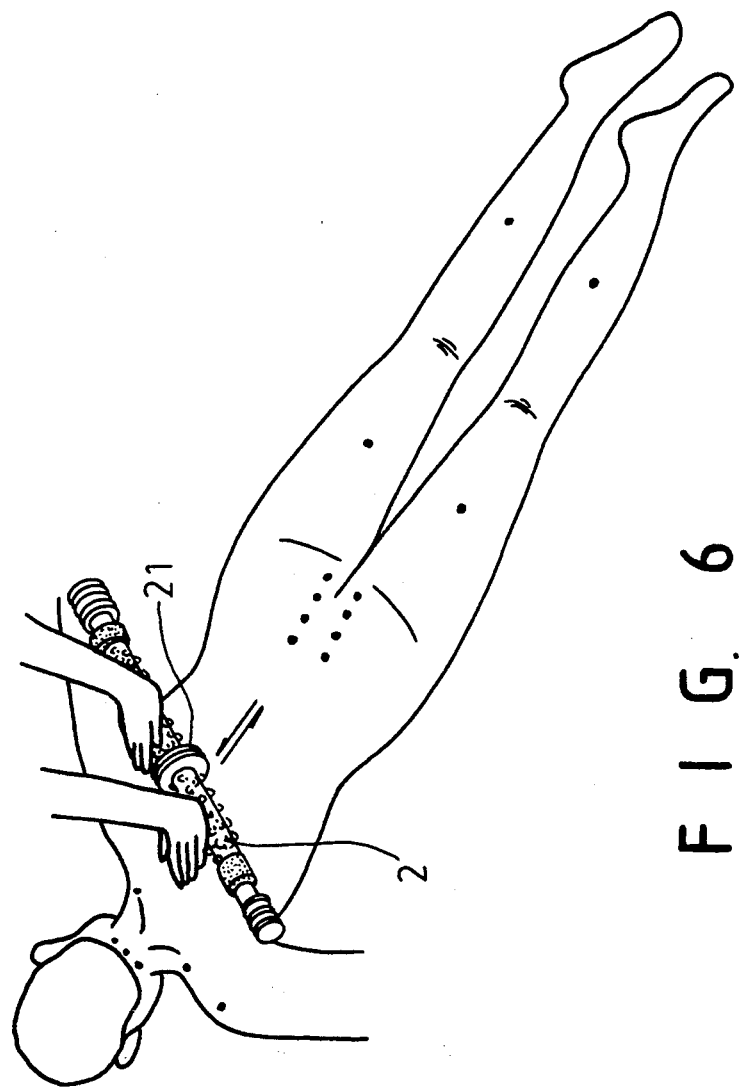
FIG. 6 is a third working view of the present invention.

FIG. 5 shows a second working view of the present invention, wherein the present invention is applied to a motor cycle. FIG. 6 shows a third working view of the present invention which will massage the hands of a user at the same time when the back of a person is massaged.

Although the present invention has been described with a certain degree of particularity, it is understood that the present disclosure is made by way of example only and that numerous changes in the detail of construction and the combination and arrangement of parts may be resorted to without departing from the spirit and scope of the invention as hereinafter claimed.

I claim:

1. A massaging sleeve comprising:
   a pair of half-cylindrical members that matingly engage to form a cylindrical member and have a body with a flange at both ends, said body being formed with a plurality of equidistant protuberances some of which are solid while others of which hollow in structure, said flange being provided with a recess;
   a packing fitted into the recess of said flange;
   a pair of pads each covering one of said half-cylindrical members and having a plurality of equidistant holes adapted to receive the protuberances of said cylindrical member;
   a plurality of magnets each fitted into one of the hollow protuberances of said cylindrical member; and
   two retainer rings for keeping said pads on said half-cylindrical members together.

* * * * *